United States Patent
Francois et al.

(10) Patent No.: US 9,833,546 B2
(45) Date of Patent: Dec. 5, 2017

(54) METHOD OF MANUFACTURING AN IMPLANTABLE FILM AND PROTHESIS COMPRISING SUCH A FILM

(71) Applicant: Sofradim Production, Trévoux (FR)

(72) Inventors: Sebastien Francois, Jassans-Riottier (FR); Nicolas Prost, Orlienas (FR); Suzelei Montanari, Trévoux (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 15/116,836

(22) PCT Filed: Feb. 18, 2015

(86) PCT No.: PCT/EP2015/053397
§ 371 (c)(1),
(2) Date: Aug. 5, 2016

(87) PCT Pub. No.: WO2015/124615
PCT Pub. Date: Aug. 27, 2015

(65) Prior Publication Data
US 2017/0165399 A1    Jun. 15, 2017

(30) Foreign Application Priority Data
Feb. 19, 2014   (FR) .................................... 14 51306

(51) Int. Cl.
| | |
|---|---|
| *A61L 27/50* | (2006.01) |
| *A61L 31/14* | (2006.01) |
| *A61L 27/34* | (2006.01) |
| *A61L 31/04* | (2006.01) |
| *A61L 2/08* | (2006.01) |
| *D06B 3/10* | (2006.01) |
| *D06N 3/00* | (2006.01) |

(52) U.S. Cl.
CPC .............. *A61L 27/34* (2013.01); *A61L 2/081* (2013.01); *A61L 27/50* (2013.01); *A61L 31/044* (2013.01); *A61L 31/14* (2013.01); *D06B 3/10* (2013.01); *D06N 3/00* (2013.01); *A61L 2420/02* (2013.01); *D06B 2700/27* (2013.01); *D06N 2201/02* (2013.01); *D06N 2203/02* (2013.01); *D06N 2205/16* (2013.01); *D10B 2331/04* (2013.01); *D10B 2509/00* (2013.01)

(58) Field of Classification Search
CPC .......... A61L 27/50; A61L 31/044; A61L 31/14
USPC ............................................ 427/2.1; 424/424
See application file for complete search history.

(56) References Cited

U.S. PATENT DOCUMENTS

| | | | |
|---|---|---|---|
| 4,931,546 A | 6/1990 | Tardy et al. | |
| 6,596,304 B1 * | 7/2003 | Bayon .................. | A61L 15/325 424/444 |
| 2010/0016872 A1 * | 1/2010 | Bayon .................. | A61F 2/0063 606/151 |
| 2013/0078285 A1 * | 3/2013 | Ladet ..................... | A61L 27/20 424/400 |

FOREIGN PATENT DOCUMENTS

| | | |
|---|---|---|
| FR | 2601371 A1 | 1/1988 |
| WO | WO 90/09769 A1 | 9/1990 |
| WO | 9906080 A1 | 2/1999 |
| WO | WO 2009/156866 A2 | 12/2009 |

OTHER PUBLICATIONS

International Search Report for PCT/EP15/053397 dated Jul. 15, 2015 (10 pages).

* cited by examiner

*Primary Examiner* — Cachet Sellman

(57) ABSTRACT

A method for manufacturing an implantable film and a prosthesis comprising such a film The present invention relates to a method for manufacturing a non porous film intended to be implanted in the human body, said method comprising the following steps: preparation of a first film, called intermediate film, via gelling of a starting solution comprising at least one polymer selected in the group consisting of collagen, glycosaminoglycans, and mixtures thereof, immersion of said intermediate film in an alkaline composition comprising at least one $C_1$-$C_4$ alcohol, drying of the film obtained at the end of the immersing step. The invention also relates to a method for manufacturing a prosthesis comprising a textile support and such a film.

21 Claims, No Drawings

METHOD OF MANUFACTURING AN IMPLANTABLE FILM AND PROTHESIS COMPRISING SUCH A FILM

CROSS-REFERENCE TO RELATED APPLICATIONS

This application is a National Stage Application of PCT/EP15/053397 under 35USC §371 (a), which claims benefit of and priority to French Patent Application Serial No. 14/51306 filed Feb. 19, 2014, the disclosures of each of the above-identified applications are hereby incorporated by reference in their entirety.

BACKGROUND

1. Technical Field

The present invention concerns a method for manufacturing a particularly resistant film, based on a polymer selected in the group consisting of collagen and glycosaminoglycans, intended to be implanted in the human body, for example for a use as a barrier for the prevention of post-surgical adhesions, in implants such as wall reinforcements in the treatment of hernia.

2. Description of Related Art

Abdominal wall reinforcements are often based on a biocompatible textile support, which is generally porous in order to promote the cell colonization.

Textile supports are intrinsically adhesiogenic and fibrogenic, irrespective of the nature of the tissues with which they are put in contact. This property expressed with respect to the support tissues (muscles, aponeuroses, fascias, etc.) constitutes an indispensable prerequisite for the quality of the result. In contrast, with respect to other more fragile structures, the presence of a textile support during the initial cicatricial inflammation promotes the establishment of dense fibrous links, where only loose links existed, such as those that the interstitial conjunctive tissues procure for the extra-peritoneal organs, and where no link was present for the intra-peritoneal organs. Hence, the porous nature of the textile supports is often the cause of the development of post-surgical erosions and adhesions.

Post-surgical adhesions comprise all non-anatomical fibrous links, fortuitously induced by a surgical act during the normal process of healing. They can cause syndromes which can be mainly classified into chronic pain, occlusive syndromes and female infertility. Moreover, they substantially increase the risks of wrong track during a reoperation, while extending surgery duration, since the prior dissection may be in such cases very tedious.

To remedy this problem, it was suggested to render at least one face of these reinforcement prostheses completely smooth during the initial inflammatory phase, and therefore not favorable to the generation of adhesions. To do this, a physical barrier is interposed between the structures which are not intended to adhere to each other.

WO99/06080 describes a porous textile support intended for a use in parietal surgery, for the repair of eventrations or hernias, a face of which is superficially covered by a smooth resorbable film, the other face being left free for an intimate and early tissue integration. The film of WO99/06080 is obtained via gelling of a starting solution comprising collagen.

Nevertheless, it was found that the films of the prior art used as a barrier for the prevention of post-surgical adhesions may lack mechanical strength and resistance, and may tear up.

Moreover, in the surgical field, it is also possible to use films, which may be transparent, in order to reinforce a portion of an implant where it is desired to practice sutures to secure this implant in the patient's body.

There remains thus a need for a film, preferably smooth, intended to be implanted in the human body, usable as a barrier for the prevention of post-surgical adhesions in an implant, such as abdominal wall reinforcement prostheses, or as a reinforcing element of an area of sutures, having a good elasticity and a good mechanical strength, in particular good tensile strength.

SUMMARY

The Applicant has found that by introducing, in a method for preparing a non porous film obtained by the gelling of a starting solution comprising collagen or a glycosaminoglycan, a step of immersing the film in a specific composition, it was possible to finally obtain a particularly resistant film. In particular, such a film is much more resistant and shows a greater tensile strength and elasticity than a film manufactured by gelling of a starting solution comprising collagen but not having undergone said immersing step.

DETAILED DESCRIPTION

The present invention relates to a method for manufacturing a non porous film intended to be implanted in the human body, said method comprising the following steps:

a°) preparation of a first film, called intermediate film, via gelling of a starting solution comprising at least one polymer selected in the group consisting of collagen, glycosaminoglycans, and mixtures thereof, b°) immersion of said intermediate film in an alkaline composition comprising at least one $C_1$-$C_4$ alcohol, c°) drying of the film obtained at the end of the immersing step.

The present invention also relates to a method for manufacturing a prosthesis comprising a textile support and a non porous film associated with one face of this textile support comprising the following steps:

i°) preparation of an intermediate film via gelling of a starting solution comprising at least one polymer selected in the group consisting of collagen, glycosaminoglycans, and mixtures thereof, and application of a face of the textile support on said intermediate film before the end of the gelling in order to associate said textile support with said intermediate film, ii°) immersion of the intermediate film associated with the textile support in an alkaline composition comprising at least one $C_1$-$C_4$ alcohol, iii°) drying of the film associated with the textile support obtained at the end of the immersing step.

The film obtained by the method according to the invention is non porous and has mechanical properties allowing it to have a good tensile strength. The film obtained by the method of the invention shows a flexibility allowing it to be easily manipulated and handled by a surgeon. The flexibility of the film obtained by the method of the invention allows it to conform either to the surrounding biological tissues once implanted or to the shape of another implant with which it may be associated for example. The film of the method according to the invention can thus be used for example as a reinforcing member of the suture area of another implant. The film of the method according to the invention may alternatively be used in combination with a textile support as a barrier for the prevention of post-surgical adhesions.

The method according to the invention comprises a first step of gelling of a starting solution comprising at least one polymer selected in the group consisting of collagen, glycosaminoglycans, and mixtures thereof. During this step, a first film, called intermediate film in the present application, is obtained.

Collagen is a natural protein having a good biocompatibility. It is present in the vertebrates in the form of extracellular fibers or networks, for example in the skin, the cartilage, and the blood vessels. The collagen usable according to the present invention is preferably selected from collagen of animal origin, collagen of human origin, such as for example the human placenta collagen, collagen obtained by genetic recombination means, and mixtures thereof.

In one embodiment of the invention, the collagen used is a collagen of animal origin. The collagen of animal origin is preferably bovine or porcine collagen of type I.

The collagen of human origin or the collagen obtained by genetic recombination is preferably collagen of type I, of type III, of type IV, or mixtures thereof.

In one embodiment of the invention, native collagen, solubilized at an acidic pH or after treatment by digestion with the pepsin, is used.

According to another embodiment of the invention, oxidized collagen is used, for example modified by oxidative cutting.

To this end, periodic acid or one of its salts can be used according to the technique described by Tardy and coll. (1986) in the application FR 2 601 371-A1. According to the technique described in this application, an acidic collagen solution is subjected to the action of the periodic acid or one of its salts by mixing with a solution of this acid or salt at a molar concentration comprised between 1 and $10^{-5}$; preferably between $5 \times 10^{-3}$M and $10^{-1}$M, at a temperature near ambient temperature, for a time ranging from 10 minutes to 72 hours. Still according to this technique, an acidic collagen solution whose concentration is comprised between 5 and 50 g/l is used. The collagen concentration is preferably 30 g/l. This treatment causes cuttings in some constituents of the collagen which are the hydroxylysine and the sugars and thus creates reactive sites without causing the crosslinking. The oxidized collagen thus prepared in solution is heated at a temperature of 37° C. or slightly higher. As a result, the helical structure of the collagen is denatured, at least partially.

In one alternative of the invention, the oxidation step may be eliminated and the initial solution of non oxidized collagen may be directly used.

Preferably, the collagen used is a collagen of type I, extracted from animal dermis, by solubilization at an acidic pH or by digestion with the pepsin and purified by saline precipitations; it can be used either after oxidation by the periodic acid, or at the non oxidized native state.

By "glycosaminoglycan" is meant, within the meaning of the present application, complex polysaccharides having repeating units, either of a same saccharide subunit or of different saccharide subunits. Examples of glycosaminoglycans are dermatan sulfate, hyaluronic acid, chondroitin sulfates, chitin, heparin, keratan sulfate, keratosulfate, and derivatives thereof. Among the derivatives of glycosaminoglycans, partially or completely deacetylated versions of these compounds can be cited, such as chitosan or deacetylated hyaluronic acid for example.

According to the first step of the method according to the invention, a starting solution is prepared, comprising a polymer which may be collagen, glycosaminoglycan and/or a mixture of these compounds. The polymer is generally solubilized in the solution.

In one embodiment of the invention, the polymer is collagen. Preferably, the starting solution comprises oxidized collagen.

The starting solution may comprise, in addition to the polymer selected from collagen, glycosaminoglycans and mixtures thereof, a plasticizer. The plasticizer can be selected from glycerol, polyethylene glycol and mixtures thereof. For example, the plasticizer is glycerol.

In one embodiment of the method according to the invention, the starting solution is a solution of solubilized oxidized collagen comprising glycerol.

In one embodiment of the invention, the pH of the starting solution is acidic, preferably ranging from 3.4 to 3.6, preferably is 3.5. Such a pH allows good solubilization of the different compounds, for example of a mixture of collagen and chitosan.

In one embodiment of the method according to the invention, the starting solution is a solution of solubilized oxidized collagen comprising glycerol, having a pH of about 3.5.

The method according to the invention comprises at least the gelling of the starting solution in order to obtain an intermediate film. This gelling can be done in two steps as described in WO99/06080. A part of the starting solution is for example spread on an inert support and is left to dry, for one hour for example. Once this first layer has gelled, the rest of the starting solution is spread over the first layer already gelled, and it is left to dry, for example also for one hour.

In another embodiment of the method according to the invention, the gelling is done in one single step. All of the starting solution prepared is spread on an inert support and is left to dry until a film is obtained.

According to the method for manufacturing a prosthesis according to the invention, one face of the textile support is applied on the intermediate film before the end of the gelling step in order to associate the textile support with the intermediate film.

The film obtained after the gelling step, or intermediate film, may optionally be dried under a laminar flow before the immersing step in the alkaline composition. Thus, for example, the intermediate film may be dried under a laminar flow at 37° C. for 20 h.

When the intermediate film is associated with a textile support to form a prosthesis, the whole of the prosthesis may optionally be dried under a laminar flow before the immersing step in the alkaline composition.

According to a second step of the method of the invention, the intermediate film, dried or not, optionally associated with a textile support to form a prosthesis, is then immersed in an alkaline composition comprising at least one $C_1$-$C_4$ alcohol. This second step allows reducing the volume of the film. In particular, this step allows "compacting" the intermediate film by expelling therefrom a part of the water it contained at the end of the gelling step and of the optional drying step under laminar flow. For example, the present step allows reducing the thickness of the film of 30%. It is assumed that during this step, the interstitial spaces between the chains of the polymer are reduced, the chains getting closer to each other.

In one embodiment of the method according to the invention, the $C_1$-$C_4$ alcohol is selected from methanol, ethanol, propanol, 1,2 propanediol, isopropanol, butanol, and mixtures thereof. For example, the alcohol is ethanol.

In one embodiment of the method according to the invention, the amount of $C_1$-$C_4$ alcohol ranges from 85% to 99%, preferably from 90% to 91%, by weight, with respect to the weight of the alkaline composition. Such amount of $C_1$-$C_4$ alcohol allows a particularly effective reduction in the volume of the intermediate film at the end of the immersing step.

In one embodiment of the method according to the invention, the alkaline composition comprises sodium hydroxide (NaOH). For example, sodium hydroxide is present in an amount ranging from 0.010 to 0.030 mol/L. The sodium hydroxide amount allows varying the elastic properties and the mechanical strength of the resulting film.

In one embodiment of the method according to the invention, the alkaline composition further comprises a plasticizer. The presence of a plasticizer in the alkaline composition allows preserving a certain elasticity to the final film, allowing its easy handling. As a plasticizer usable in the alkaline composition of the method according to the invention, glycerol, polyethylene glycol and mixtures thereof can be cited. For example, the plasticizer is glycerol.

The plasticizer may be present in the alkaline composition of the method according to the invention in an amount ranging from 4% to 7%, preferably from 5% to 6%, by weight, with respect to the weight of the composition.

In one embodiment of the method according to the invention, the immersing time of the intermediate film, optionally associated with a textile support to form a prosthesis, in the alkaline composition ranges from about 60 min to about 180 min, for example is about 60 min. Such an immersing time allows to control the neutralization of the film and to obtain the desired final mechanical properties.

The film obtained at the end of the immersing step has a reduced volume with respect to the intermediate film obtained in the preceding step. For example, the thickness of the film was reduced by 30% during the immersing step. Thus, the immersing step described above performs a kind of chemical compaction of the intermediate film.

By this chemical compaction, a part of the water present in the intermediate film obtained after gelling and optionally drying under laminar flow is expelled. Thus, the film obtained after the step of chemical compaction comprises a percentage of water significantly lower than that of the film before chemical compaction and it also occupies a smaller volume.

In one embodiment of the method according to the invention, the film thus compacted, i.e. obtained at the end of the immersing step described above, is washed before drying. For example, the film may be washed with water in order to remove the residual salts therefrom. The film is washed until obtaining a washing solution having a pH acceptable for an implantation of the film in the human body, for example a pH ranging from 1 to 8.

In one embodiment of the method according to the invention, the washed and compacted film is then dried under a laminar flow for example for several hours.

In one embodiment of the method of the invention, the dried film is sterilized by gamma irradiation. It is assumed that during this step, the polymer chains are reorganized, further reinforcing the mechanical properties of the final film.

The film thus obtained by the method of the invention has excellent mechanical properties, and in particular an excellent tensile strength. The film obtained by the method according to the invention may be directly used to be implanted in the human body, for example to reinforce a suture area of another implant to be secured to biological tissues, or as an anastomosis reinforcement intended to be stapled.

The film obtained according to the method of the invention has a smooth, non-porous aspect and it can also be associated with a textile support to form a barrier for the prevention of post-surgical adhesions. The film may be prepared independently of the textile support and then be associated therewith subsequently. Alternatively, the film of the method according to the invention may be associated with the textile support during the steps of its manufacture as described above.

The textile support may be any biocompatible textile. For example, the textile support may be openwork to allow a better cell colonization of the face which is not coated by the film of the method according to the invention.

The present invention and its advantages will appear in detail from the following examples.

Example 1

Two films were prepared as follows:

A solution of solubilized oxidized collagen at 2.7% (w/w) is prepared, with 0.55% (w/w) of glycerol, and a pH of 3.5. About 70% of the volume of the solution is spread over an inert support to form a first layer. After leaving this first layer to dry for about 1 h and until it is in gel form, the 30% of the remaining volume of the starting solution is applied to form a second layer. This second layer is left to dry for about 1 h.

The films are then submitted to a drying step under a laminar flow of 1 m/s, 37° C. and 40% of humidity, for 20 h.

The first (comparative) film, hereinafter called F1, is submitted to a sterilization by gamma irradiation (radiation ranging from 25 kGy to 40 kGy) then is left for three days in an oven at 40° C.

The second film (according to the invention), hereinafter called F2, is immersed in an alkaline composition A of the following formulation:

| Composition A | |
|---|---|
| Component | % By weight, with respect to the weight of the composition |
| Ethanol | 90.50 |
| Glycerol | 5.91 |
| Water | 2.36 |
| Sodium hydroxide 1N | 1.23 |

The film F2 is immersed in this composition for about 60 min.

During this step, a portion of the water present in the film is expelled from the film by ethanol.

After this step, the film F2 therefore holds less humidity and occupies a smaller volume. It is thus found that the film F2 has lost 30% of its thickness during this step.

The film F2 is then washed with water in order to remove the residual salts.

Then, the film F2 is again submitted to a drying step under laminar flow of 1 m/s, 37° C. and 40% of humidity, for 20 h.

The film F2 is then submitted to a sterilization by gamma irradiation (radiation ranging from 25 kGy to 40 kGy) and then left for three days in an oven at 40° C., in the same way as for the comparative film F1.

The maximum elastic force was then measured for a linear behavior of the films F1 and F2, that is, the force at 18% of deformation, by submitting these films to the mechanic tensile strength test according to the following protocol:

Test samples of "dog bone" shape type of 11.5 cm×0.5 cm are cut for each film.

Each test sample is then tested on a tensile bench "HT 400 Pneumatic Grip Controller" ECME 0702

The measurement parameters are as follows:
Scale F: 5N
Scale D: 100 mm
Speed: 50 mm/min
Elongation length: 40 mm
Elongation 1: 20%
Elongation 2: 18%
Breaking Sensor: 100%
Preload: 0.005N For this test, the test sample is placed in a gripper and then immersed in a solution of sodium chloride at 0.9% for a time ranging from 5 to 7 min. The test sample is placed between the jaw and the gripper. The apparatus then moves the jaw away from the gripper. The force is measured until the test sample breaks.

The results are given in the following table:

| Film | Force at 18% of deformation in N + standard deviation |
| --- | --- |
| F1 (comparative) | 0.19 ± 0.018 |
| F2 (invention) | 0.344 ± 0.042 |

Thus, the film F2 obtained by the method according to the invention has a tensile strength much greater than that of the film F1 of the prior art.

The film F2 has a smooth, non-porous aspect. The film F2 can be directly used and implanted in the human body, as a reinforcement member of a suture area of another implant. Alternatively, it may be associated with a biocompatible textile support to form a barrier for the prevention of post-surgical adhesions for a prosthesis for repairing a hernia, for example.

Example 2

Films of the invention were manufactured by the same method as in Example 1, by varying the composition of the alkaline composition A, by preparing the compositions A1, A2, A3 and A4 as indicated in the table below (the amounts are given in percent by weight, with respect to the weight of the composition):

| | Composition | | | |
| --- | --- | --- | --- | --- |
| | A1 | A2 | A3 | A4 |
| Ethanol | 90.48 | 90.46 | 90.44 | 90.46 |
| Glycerol | 5.90 | 5.90 | 5.90 | 5.90 |
| Water | 1.77 | 1.18 | 0.59 | 0.00 |
| Sodium hydroxide 1N | 1.84 | 2.46 | 3.07 | 3.68 |

The immersing time of the film in each composition is identical, namely about 60 min.

The resulting film after immersion in the composition Ai, for i ranging from 1 to 4, is called FAi.

The concentration in mol/L of sodium hydroxide (NaOH) used in the alkaline composition used for the different films F2 (Example 1) and FAi is as indicated in the following table:

| Film | NaOH concentration in mol/L in the alkaline composition |
| --- | --- |
| F2 (Example 1) | 0.010 |
| FA1 | 0.015 |
| FA2 | 0.020 |
| FA3 | 0.025 |
| FA4 | 0.030 |

The films FA1-FA4 were submitted to the mechanical tensile strength test described in the Example 1. The results are the following:

| Film | Force at 18% of deformation in N+ standard deviation |
| --- | --- |
| F2 (Example 1) | 0.344 ± 0.042 |
| FA1 | 0.513 ± 0.004 |
| FA2 | 0.692 ± 0.042 |
| FA3 | 1.073 ± 0.059 |
| FA4 | 1.217 ± 0.048 |

Thus, the variation of the molar concentration of sodium hydroxide in the alkaline composition of the immersing step of the method according to the invention allows varying the mechanical properties of the resulting film.

The films FA1-FA4 have a smooth and non-porous aspect. They can be directly used and implanted in the human body as members of reinforcement of a suture area of another implant. Alternatively, they may be associated with a biocompatible textile support to form a barrier for the prevention of post-surgical adhesions for a prosthesis for repairing a hernia, for example.

Example 3

A solution of solubilized oxidized collagen at 2.7% (w/w) was prepared, with 0.55% (w/w) of glycerol, and a pH of 3.5. About 70% of the volume of the solution is spread over an inert support to form a first layer. When this first layer is gelled, the 30% of the remaining volume of the starting solution is applied to form a second layer.

A textile, for example of monofilament of polyethylene terephthalate (PET), is then deposited on this second layer before the end of the gelling of this second layer. The textile therefore becomes superficially anchored in the second layer of the film while it is in the process of gelling.

The prosthesis consisting of the film associated with the textile is then dried under a laminar flow of 1 m/s, 37° C. and 40% of humidity, for at least 16 h.

The prosthesis is then immersed in an alkaline composition B of the following composition:

| Composition B | |
| --- | --- |
| Component | % By weight, with respect to the weight of the composition |
| Ethanol | 90.50 |
| Glycerol | 5.91 |

-continued

| Composition B | |
|---|---|
| Component | % By weight, with respect to the weight of the composition |
| Water | 2.36 |
| sodium hydroxide 1N | 1.23 |

The prosthesis is immersed in this composition for about 60 min.

During this step, a portion of the water present in the film of the prosthesis is expelled from the film by the ethanol.

After this step, the film holds thus less humidity and occupies a smaller volume. It is noted that the film thickness was reduced by about 30%.

The prosthesis is then washed with water in order to remove residual salts therefrom until obtaining a washing solution having a pH compatible with an implantation of the prosthesis in the human body. The prosthesis is then dried under a laminar flow of 1 m/s, 37° C. and 40% of humidity, for at least 16 h.

The prosthesis is then submitted to a step of sterilization by gamma irradiation (radiation ranging from 25 kGy to 40 kGy).

After sterilization, the prosthesis is left three days at a temperature of 40° C. for the structuration of the film. It is assumed that during this step, the polymer chains are reorganized, further reinforcing the mechanical properties of the final film.

A prosthesis usable as abdominal wall reinforcement is obtained, which is particularly effective for the prevention of post-surgical adhesions on the face of the textile provided with the non porous film obtained by the method according to the invention.

What is claimed is:

1. A method for manufacturing a non porous film intended to be implanted in the human body, said method comprising the following steps:
    a°) preparing an intermediate film via gelling of a starting solution comprising at least one polymer selected in the group consisting of collagen, glycosaminoglycans, and mixtures thereof,
    b°) immersing said intermediate film in an alkaline composition comprising at least one $C_1$-$C_4$ alcohol,
    c°) drying said intermediate film obtained at an end of said immersing step.

2. The method according to claim 1, wherein said starting solution comprises oxidized collagen.

3. The method according to claim 2, wherein said starting solution further comprises glycerol.

4. The method according to claim 1, wherein said $C_1$-$C_4$ alcohol is selected from methanol, ethanol, propanol, 1,2 propanediol, isopropanol, butanol and mixtures thereof.

5. The method according to claim 1, wherein said $C_1$-$C_4$ alcohol comprises ethanol.

6. The method according to claim 1, wherein an amount of the $C_1$-$C_4$ alcohol ranges from 85% to 99% by weight, with respect to a weight of said alkaline composition.

7. The method according to claim 1, wherein an amount of the $C_1$-$C_4$ alcohol ranges from 90% to 91% by weight, with respect to a weight of said alkaline composition.

8. The method according to claim 1, wherein said alkaline composition further comprises sodium hydroxide.

9. The method according to claim 8, wherein said sodium hydroxide is present in said alkaline composition in an amount ranging from 0.010 to 0.030 mol/L.

10. The method according to claim 8, wherein said alkaline composition further comprises at least one plasticizer.

11. The method according to claim 10, wherein said at least one plasticizer comprises glycerol.

12. The method according to claim 1, wherein immersing said intermediate film in said alkaline composition comprises an immersing time ranging from about 60 min to about 180 min.

13. The method according to claim 1, wherein said starting solution comprises an acidic pH ranging from 3.4 to 3.6.

14. The method according to claim 1, wherein said intermediate film is first dried under a laminar flow before said step of immersing said intermediate film in said alkaline composition.

15. The method according to claim 1, wherein drying said intermediate film obtained at said end of the immersing step is carried out by subjecting said intermediate film to a laminar flow.

16. The method according to claim 1, further comprising sterilizing said intermediate film, obtained after said drying step, by gamma irradiation.

17. The method according to claim 1, further comprising washing said intermediate film obtained at an end of said immersing step and before said drying step.

18. A method for manufacturing a prosthesis comprising a textile support and a non porous film associated with a face of said textile support comprising the following steps:
    i°) preparing an intermediate film via gelling of a starting solution comprising at least one polymer selected in the group consisting of collagen, glycosaminoglycans, and mixtures thereof, and applying a face of said textile support on said intermediate film before an end of the gelling in order to associate said textile support with said intermediate film,
    ii°) immersing said intermediate film associated with said textile support in an alkaline composition comprising at least one $C_1$-$C_4$ alcohol,
    iii°) drying said intermediate film associated with said textile support obtained at an end of said immersing step.

19. The method according to claim 18, wherein said starting solution comprises oxidized collagen and glycerol, and an acidic pH ranging from 3.4 to 3.6.

20. The method according to claim 18, wherein said $C_1$-$C_4$ alcohol comprises ethanol and said alkaline composition further comprises sodium hydroxide.

21. The method according to claim 18, further comprising sterilizing by gamma irradiation said intermediate film obtained after said drying step, wherein drying step is carried out by subjecting said intermediate film to a laminar flow.

* * * * *